United States Patent

Sleigh et al.

[11] 4,330,539
[45] May 18, 1982

[54] NOVEL 17-AMINO-16-HYDROXY STEROIDS OF THE ANDROSTANE AND OESTRANE SERIES AND DERIVATIVES THEREOF

[75] Inventors: Thomas Sleigh, Wishaw; David S. Savage, Glasgow, both of Scotland; Filippus J. Zeelen, Heesch, Netherlands

[73] Assignee: Akzo nv, Oss, Netherlands

[21] Appl. No.: 230,042

[22] Filed: Jan. 29, 1981

[51] Int. Cl.³ .............................................. A61K 31/56
[52] U.S. Cl. .................... 424/238; 424/243; 260/397.4; 260/397.5
[58] Field of Search ............... 260/397.3, 397.4, 397.5; 424/238, 243

[56] References Cited

U.S. PATENT DOCUMENTS 4,144,334  3/1979  Petzoldt et al. .................. 260/397.4

*Primary Examiner*—Elbert L. Roberts
*Attorney, Agent, or Firm*—Abelman, Frayne & Rezac

[57] ABSTRACT

New and pharmacologically useful 17-amino-16-hydroxy-steroids of the androstane and oestrane series are disclosed having the formula I:

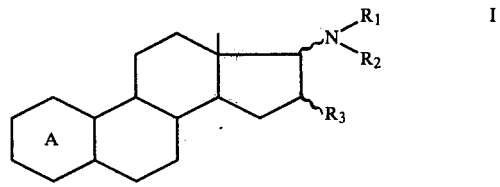

and pharmaceutically acceptable non-toxic acid addition salts thereof, wherein:

$R_1$ = H or hydrocarbyl of one to six carbon atoms (preferably lower alkyl, such as methyl);
$R_2$ = H or hydrocarbyl of one to six carbon atoms (preferably lower alkyl, such as methyl);
$R_3$ = a free, esterified or etherified hydroxyl group;

ring A inclusive carbon atoms 6 and 9 has one of the following configurations:

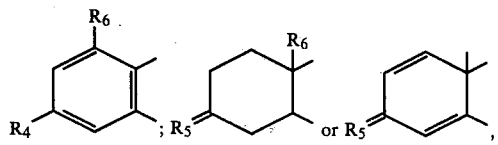

in which
$R_4$ = a free, esterified or etherified hydroxyl group;
$R_5$ = O or H($R_7$), wherein $R_7$ is a free, esterified or etherified hydroxyl group;
$R_6$ = H or methyl; and
the dotted lines represent an optional double bond in 4,5- or 5,6-position;

as well as the enantiomers and racemates of these steroids.

The novel compounds have antiarrhythmic properties.

9 Claims, No Drawings

NOVEL 17-AMINO-16-HYDROXY STEROIDS OF THE ANDROSTANE AND OESTRANE SERIES AND DERIVATIVES THEREOF

This invention relates to novel 17-amino-16-hydroxy steroids of the androstane and oestrane series and derivatives thereof, to processes for their preparation and to pharmaceutical compositions containing these compounds as active component.

In British Specification 1,108,563 amino steroids of the androstane, oestrane and pregnane series are described, having a hydroxyl or acyloxy group in 2$\beta$-position and a tertiary amino group in 3$\alpha$-position. Some of these compounds have been found to possess anti-arrhythmic activity. However, at therapeutic dose levels these compounds also exhibit undesirable activities, such as convulsant activity and local anaesthetic activity which precludes their clinical application.

In British Specification 1,439,605 amino steroids of the androstane, oestrane and pregnane series are described, having a hydroxyl or acyloxy group in 2$\beta$-position and a primary amino group in 3$\alpha$-position. These compounds have anti-arrhythmic properties and are virtually devoid of convulsant and local anaesthetic activities.

Surprisingly, it was found that novel steroids of the androstane and oestrane series, substituted in 17-position with a primary, secondary or tertiary amino group and in 16-position with a free, esterified or etherified hydroxyl group, are potent anti-arrhythmic agents.

Therefore, the present invention relates to novel steroids of the androstane and oestrane series having the formula I:

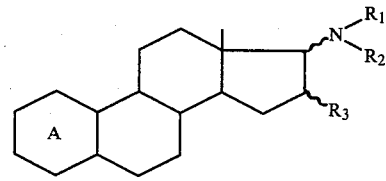

and pharmaceutically acceptable non-toxic acid addition salts thereof, wherein:
$R_1$ = H or hydrocarbyl of one to six C-atoms, preferably lower alkyl, such as methyl;
$R_2$ = H or hydrocarbyl of one to six C-atoms, preferably lower alkyl, such as methyl;
$R_3$ = a free, esterified or etherified hydroxyl group, ring A inclusive carbon atoms 6 and 9 has one of the following configurations:

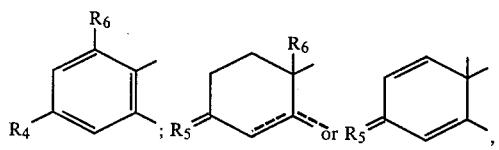

in which
$R_4$ = a free, esterified or etherified hydroxyl group;
$R_5$ = O or H($\beta R_7$), wherein $R_7$ is a free, esterified or etherified hydroxyl group;
$R_6$ = H or methyl; and the dotted lines represent an optional double bond in 4,5- or 5,6-position;
as well as the enantiomers of these compounds and racemic mixtures thereof.

The invention also relates to pharmaceutical compositions containing a pharmaceutically effective amount of one or more of the novel compounds indicated hereinbefore.

A special group of compounds is the group having formula II:

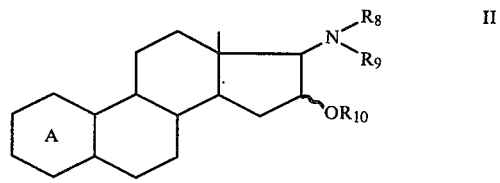

and pharmaceutically acceptable non-toxic acid addition salts thereof, wherein:
$R_8$ = H or methyl, and is preferably methyl;
$R_9$ = H or methyl, and is preferably H;
$R_{10}$ = H or lower alkanoyl of one to four carbon atoms, and is preferably H, while $OR_{10}$ is preferably in $\alpha$-position; ring A has one of the following configurations:

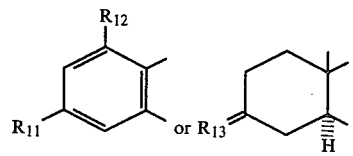

in which
$R_{11}$ = OH, alkanoyloxy (1-6 C) or Oalkyl (1-4 C), preferably OH; $R_{12}$ = H or $CH_3$; $R_{13}$ = O, H($\beta$OH) or H($\beta$-alkanoyloxy (1-4 C)), preferably O;
as well as the enantiomers and racemates.

The novel compounds have antiarrhythmic properties, have no or minimal and transient haemodynamic effects, and do not cause CNS-stimulation in the dosages required. They also have prophylactic effect and decrease infarctsize.

The compounds according to the invention can be prepared by methods employing steps known or obvious to those skilled in the art.

The methods generally comprise the use of 16,17-epoxides as starting materials or intermediates, the $\alpha$-epoxides leading in general to 17$\beta$-amino compounds and the $\beta$-epoxides to 17$\alpha$-amino compounds. These methods generally give the trans-amino alcohols, i.e. 17$\alpha$-amino-16$\beta$-hydroxy and 17$\beta$-amino-16$\alpha$-hydroxy compounds. The 17$\beta$-amino-16$\alpha$-hydroxy compounds can be converted into the $\beta$-cis-amino-alcohols, i.e. 17$\beta$-amino-16$\beta$-hydroxy compounds, by an oxidation-reduction sequence, wherein 16$\alpha$-hydroxy is first oxidized to 16-oxo, which group is then reduced to 16$\beta$-hydroxy with a complex metal hydride such as sodium borohydride. However, also other routes for preparing the compounds of the present invention are available, details of which will be indicated below.

The 16$\alpha$,17$\alpha$-epoxides to be used as starting materials may be prepared, for example, from the corresponding 17-ketones by enol acylation and treating the thus obtained $\Delta^{16}$-17-acyloxy steroid with a peracid, such as peracetic acid, perphtalic acid or perbenzoic acid, so as to obtain a 16$\alpha$,17$\alpha$-epoxy-17$\beta$-acylate. The enol acylation can be performed, for example, by reacting the 17-ketone with a isopropenyl acylate, such as isopropenyl acetate, in the presence of an acid catalyst. Esterifiable hydroxyl groups, which may be present elsewhere in the molecule, for example a 3-hydroxy group, are esterified simultaneously with the enol acylation.

The 16β,17β-epoxides to be used as starting materials may be prepared, for example, from the corresponding $\Delta^{16}$-compounds via the halohydrine by reacting the $\Delta^{16}$-compound with an organic N-halo compound, e.g. N-bromo acetamide or N-chloro succinimide, in a suitable solvent such as dimethylsulphoxide and converting the 17α-halo-16β-hydroxy compound thus obtained with alkali, e.g. potassium hydroxide, into the 16β,17β-epoxide.

A 16α,17α-epoxy-17β-acylate is rearranged to the corresponding 16α-acyloxy-17-ketone, for example with perchloric acid in acetic acid. The 16α-acyloxy-17-ketone is reacted with ammonia or an alkylamine in a suitable solvent, e.g. ethanol, to give the corresponding 16α-acyloxy-17-imino or 16α-acyloxy-17-alkylimino compound, which is then reduced with a complex metal hydride, preferably sodium borohydride, to give the 17β-amino-16α-hydroxy or the 17β-alkylamino-16α-hydroxy compound. By reacting a 16α-acyloxy-17-ketone with hydroxyl-amine in a suitable solvent, e.g. ethanol, preferably in the presence of sodium acetate, the 16α-acyloxy-17-oxime is obtained, which by hydrogenetaion, preferably in the form of the acetylated derivative, the 17-acetoxime, is converted into the corresponding 17β-amino-16α-hydroxy compound. Hydrogenation, preferably under pressure, of the 17-acetoxime gives the 17β-acetamide, which on hydrolysis gives the 17β-amino compound. The reduction of the 17-acetoxime can also be performed with diborane in tetrahydrofuran, followed by alkaline hydrolysis of the intermediate 17β-acetamide to the 17β-amino compound.

For obtaining the 17β-(alkyl)amino-16β-hydroxy compound the 17β-(alkyl)amino-16α-hydroxy compound is oxidized, preferably with Kiliani reagent in acetic acid, to the corresponding 16-ketone, which is then reduced with sodium-boro-hydride to give the 17β-(alkyl)amino-16β-hydroxy compound. The Kiliani oxidation is preferably carried out with the (alkyl)amino compound in its acylated form. Acylation of the 17β-(alkyl)amino-16α-hydroxy compound provides the 17β-acyl(alkyl)amino-16α-acetate, which on selective hydrolysis with alkali gives the 17β-acyl(alkyl)amino-16α-hydroxy compound. After the oxidation and reduction step the 17β-acyl(alkyl)amino-16β-hydroxy compound is hydrolyzed with alkali to the 17β-(alkyl)amino-16β-hydroxy compound.

As described above, the reaction of a 16α-acyloxy-17-ketone with ammonia in ethanol gives a 17-imino compound. On reduction with sodium borohydride a mixture of 17β-amino-16α-hydroxy and 17α-amino-16α-hydroxy compounds is obtained. This mixture can be separated by conversion to a mixture of the acid addition salts with hydrochloric acid, from which the water-insoluble 17α-amino-16α-hydroxy-hydrochloride can be isolated easily. Treatment with alkali, e.g. a saturated potassium hydrogen carbonate solution, gives the free base.

The 17α-amino-16α-hydroxy compounds can also be prepared by starting from a $\Delta^{16}$-steroid, converting said steroid into the 16α,17α-aziridine by reaction with N-p-nitrobenzene-sulphonoxy-urethane in the presence of triethylamine and hydrolysis of the thus-obtained 16α,17α-carbethoxy-aziridine, converting the 16α,17α-aziridine into its acylate, such as the N-acetyl or N-benzoyl derivative, rearranging the N-acyl aziridine with sodium iodide/acetone to the corresponding 16α,17α-oxazoline and hydrolyzing this with acid, e.g. diluted sulphuric acid, to the 17α-amino-16α-hydroxy compound in the form of its acid-addition salt. Neutralisation with base gives the free 17α-amino-16α-hydroxy compound.

When starting from a 16β,17β-epoxide, this compound is reacted with an alkali metal azide to give the corresponding 17α-azido-16β-hydroxy compound, which is converted into the 17α-amino-16β-hydroxy steroid by reduction, e.g. with hydrogen in the presence of a metal catalyst and preferably with lithium aluminiumhydride.

A 17-methylamino compound can readily be prepared from the corresponding 17-amino compound by N-formylation, e.g. by reacting with ethylformate in ethanol in the presence of sodium ethoxide, followed by reduction of the 17-formamido steroid thus-obtained, e.g. with a complex metal hydride, preferably with lithium aluminiumhydride in tetrahydrofuran.

A 17-dimethylamino compound can be obtained by repeating the above N-formylation and reduction on a 17-methylamino compound. Also, direct conversion of a 17-methylamino compound into a 17-dimethylamino compound is possible by methylation with formic acid/formalin.

A 17-isopropylamino compound can be prepared as indicated hereinbefore by condensation of a 16α-acyloxy-17-ketone with isopropylamine and reduction of the intermediate 17-imino compound with a complex metal hydride. A 17-isopropylamino compound can also be prepared by heating a 16α-hydroxy-17β-amino compound with acetone at reflux temperature for e.g. 3 days, affording the intermediate 17-isopropylidene-imino compound which can be reduced with a complex metal hydride to the desired 17β-isopropylamino-16α-hydroxy compound. Another route to this 17β-isopropylamino compound is the alkylation of a 16α-hydroxy-17β-amine with iodopropane in a suitable solvent, such as dimethylformamide, in the presence of potassium bicarbonate, usually at room temperature for several days, e.g. 4 days.

The substituents in position 3 and the double bond(s) in ring A or ring B may be present in the starting substances or may be introduced after the introduction of the vicinal amino-hydroxy substituents in ring D.

For preparing $\Delta^4$ or $\Delta^5$ compounds the double bond in 4,5- or 5,6-position is usually already present in the starting substances, e.g. 3β,16α-di-acetoxy-$\Delta^5$-androsten-17-one or 16α-acetoxy-$\Delta^4$-androstene-3,17-dione, which is then reacted as described hereinbefore to give via the 17-imino compound the corresponding 17β-(alkyl)amino-16α-hydroxy steroid. An end-product having a 3β-hydroxy-$\Delta^5$ group can be easily converted in an endproduct having a 3-oxo-$\Delta^4$ group, e.g. by Oppenauer oxidation.

Another route for obtaining the $\Delta^4$ and $\Delta^5$ compounds is starting from dehydro-epiandrosterone acetate, protecting the double bond in 5,6-position in the form of the dichloride (addition of chlorine to give the 5α,6β-dichloro compound) and then subjecting the 5α,6β-dichloro compound to a reaction sequence as described hereinbefore, e.g. enolacylating in 16,17-position, reacting the enol acylate with peracetic acid in chloroform to give the 16α,17α-epoxy-17-acetate, rearranging the epoxy-acetate with BF$_3$-etherate in toluene to give the corresponding 16α-acetoxy-17-ketone, which is then reacted as described to give via the 17- imino compound the corresponding 5α,6β-dichloro-17β-(alkyl)amino-16α-hydroxy steroid. Treatment of the dichloro compound with zinc dust in ethanol regenerates the Δ⁵ compound. Reaction of the 5α,6β-dichloro-3-hydroxy compound with lithiumchloride (heating for 3 hours at 110° C. in dimethylformamide) provides the corresponding Δ⁴-3-ketone.

A Δ⁴-3-ketone can readily be converted into a Δ¹,⁴-3-ketone by conventional dehydrogenation procedures, e.g. reaction with selenium dioxide or with a suitable quinone such as dichlorodicyanobenzoquinone. A very convenient procedure is the dehydrogenation with diphenylselenic anhydride in a solvent such as chlorobenzene, while temporarily protecting a primary or secondary 17-amino group by acylation, preferably with trifluoro-acetic anhydride in pyridine.

In all methods for preparing the novel compounds any hydroxy group in position 3 and/or 16 (if present), an oxo group in position 3 (if present), and the (alkyl)amino group in position 17 are temperarily protected, if required, by reversible ester- or ether-formation (hydroxy group), reversible acetal-formation (oxo group) or reversible acyl-, carbamate- or salt-formation (amino group).

Protection of the 17-(alkyl)amino group in the form of the carbamate thereof can be performed by treatment of the 17-(alkyl)amine with alkyl- or arylhaloformate, such as benzylchloroformate, giving the corresponding alkyl- or arylcarbamate. Decarboxylation can be performed by hydrogenolysis in a suitable solvent, such as acetic acid or methanol, over a novel metal, e.g. palladium, on carbon, to give back the 17-(alkyl)amine.

A hydroxy group may be acylated according to procedures well-known in the art, e.g. by reaction with an organic carboxylic acid or a functional derivative thereof, such as the anhydride or the acid chloride, in the presence of a water-binding agent or a base, such as pyridine.

Acyl groups, if present in the 3- and/or 16-position or in the amino group may be hydrolyzed, e.g. with alkali, to give the free hydroxy or amino group.

A hydroxy group, if present in the 3-position of a Δ⁴, Δ⁵ or 5αH compound, may be oxidized to the corresponding oxo group by known methods, e.g. with chromic acid in the presence of sulphuric acid or with the Oppenauer method.

A 3-oxo group, if present, may be reduced to a 3β-hydroxy group, e.g. with NaBH₄ or LiAlH₄.

An acyl group, if present in 3- and/or 16-position, may be derived from an aliphatic, cycloaliphatic, aromatic or araliphatic carboxylic acid with 1–18 carbon atoms, such as acetic acid, propionic acid, pentanoic acid, trimethyl-acetic acid, heptanoic acid, decanoic acid, dodecanoic acid, benzoic acid, β-phenyl propionic acid, cyclo-octyl acetic acid, succinic acid, and the like.

A hydroxy group, if present in the 3- and/or 16-position may be converted into an ether group derived from an aliphatic, aromatic, araliphatic or heterocyclic hydrocarbon, such as the methyl, ethyl, butyl, cyclopentyl, cyclohexyl, tetrahydro-pyranyl ether group, and the like, according to well-known procedures.

An ether group used for protection, such as for example a tetrahydropyranyl-ether group in 16-position, can be split up under acid conditions. Also acetal groups used for protection of an oxo group, such as the ethylene dioxy or the di-methyloxy group in position 3, can easily be split up by treatment with a mineral acid or a sulphonic acid at room temperature or by being gently heated with dilute acetic acid.

The preparation of the acid-addition salts of the 17-amino compounds of the invention can be performed by treatment of the amino compound with an inorganic acid such as hydrochloric acid, hydrobromic acid, phosphoric acid, nitric acid, or an organic acid, such as citric acid, pyruvic acid, succinic acid, maleic acid, sulphonic acids.

The enantiomers of the compounds of formula I can be prepared according to the same methods as described hereinbefore for the natural isomers, starting from the enentiomeric starting substances, i.e. ent-epiandrosterone, ent-oestrone and the like. Racemates of the compounds of formula I are obtained starting from racemic starting substances, e.g. dl-oestrone. These l- and dl-steroids used as starting substances are known in the art and are prepared by total synthesis.

Racemic mixtures of intermediates or end products may be resolved to give the optical antipodes in the usual way, e.g. by chromatography or crystallization.

The new compounds according to the invention may be used in the form of pharmaceutical compositions, for which purpose they are mixed with one or more pharmaceutically acceptable non-toxic carriers and/or the usual excipients suitable for enteral, i.e. oral, administration or for parenteral administration, e.g. for injection.

The effective oral dose is in the range from 0.5–25 mg/kg and the effective intravenous dose is in the range from 0.1–10 mg/kg.

The following examples illustrate the invention.

EXAMPLE I (a) 17α-Azido-16β-hydroxy-5α-androstan-3-one

A solution of sodium azide (20.5 g) in water (47.5 ml) was added to a stirred suspension of 16β,17β-epoxy-5α-androstan-3-one (25 g) in dimethyl acetamide (266 ml) and the stirred mixture was heated under reflux for 24 h., during which time a solution was obtained. The solution was cooled and water added to precipitate the product as a gum from which the aqueous was decanted. The product was dissolved in methylene dichloride and the solution was washed with water, dried (MgSO₄) and evaporated to give a yellow gum (24.5 g). Crystallisation from ether gave 17α-azido-16β-hydroxy-5α-androstan-3-one (7.4 g). Further crystallisation from ether afforded an analytical sample, m.p. 167°–170° C., [α]$_D$+45° (C 1.2).

A solution of the mother liquor (17 g) in methylene dichloride was filtered through a column (11×1½″) of silica gel. Evaporation of the eluate and crystallisation of the residue from ether gave further 17α-azido-16β-hydroxy-5α-androstan-3-one (1.3 g). Crystallisation of the mother liquor from heptane-acetone (4:1) and recrystallisation from ether gave 16α-azido-17β-hydroxy-5α-androstan-3-one as prisms (4.0 g), m.p. 165°–167° C., [α]$_D$–33° (C 1.1).

(b) 17α-Azido-16β-hydroxy-5α-androstan-3-one ethylene acetal p-Toluenesulphonic acid (0.54 g) was added to a stirred suspension of 17α-azido-16β-hydroxy-5α-androstan-3-one (8.4) in ethylene glycol (8.4 ml) and triethylorthoformate (16.8 ml) and the mixture was warmed to give a solution which was set aside at room temperature for 35 min. Aqueous sodium carbonate (5%) and water were added to give a gum, which was washed with hot water by decantation to give a solid (9.0 g). Crystallisation from ether-hexane yielded 17α-azido-16β-hydroxy-5α-androstan-3-one ethylene acetal as prisms (6.5 g), m.p. 112°–116° C., $[\alpha]_D+28°$ (C 1.1).

(c) 17α-Amino-16β-hydroxy-5α-androstan-3-one ethylene acetal

A solution of 17α-azido-16β-hydroxy-5α-androstan-3-one ethylene acetal (6.5 g) in dry tetrahydrofuran (60 ml) was added dropwise to a stirred suspension of lithium aluminium hydride (1.63 g) in tetrahydrofuran (18 ml) at 0° C. After 20 min. the cooling bath was removed and the stirred mixture was heated under reflux for 1½ h. The mixture was cooled, water was added dropwise and the solids removed by filtration through dicalite. The filter was washed with hot chloroform and the combined filtrate and washings evaporated to give a solid residue (6.0 g). Crystallisation from chloroform-ethanol gave 17α-amino-16β-hydroxy-5α-androstan-3-one ethylene acetal as prisms, m.p. 254°–258° C., $[\alpha]_D-12°$ (C 1.1).

(d) 17α-Amino-16β-hydroxy-5α-androstan-3-one.HCl

Acid hydrolysis of 17α-amino-16β-hydroxy-5α-androstan-3-one ethylene acetal gave the free 3-ketone, which was converted into its hydrochloric acid salt.

EXAMPLE II (a) 17α-Formamido-16β-hydroxy-5α-androstan-3-one ethylene acetal

Sodium (0.37 g) was added to a stirred suspension of 17α-amino-16β-hydroxy-5α-androstan-3-one ethylene acetal (5.5 g) in ethyl formate (55 ml) and ethanol (27.5 ml) and the stirred mixture was heated under reflux for 1½ h. After removal of the solvent, the residue was dissolved in chloroform and the solution was washed with water and dried (MgSO₄). Evaporation of the solvent and crystallisation of the product from chloroform-ethyl acetate gave 17α-formamido-16β-hydroxy-5α-androstan-3-one ethylene acetal (4.5 g). A second recrystallisation furnished an analytical sample m.p. 277°–280° C., $[\alpha]_D^{DMSO}+58°$ (C 1.0).

(b) 16β-Hydroxy-17α-methylamino-5α-androstan-3-one and maleate

A solution of 17α-formamido-16β-hydroxy-5α-androstan-3-one ethylene acetal (5.2 g) in dry tetrahydrofuran (182 ml) was added dropwise to a stirred suspension of lithium aluminium hydride (2.6 g) in tetrahydrofuran (78 ml) at 0° C. The cooling bath was removed and the stirred suspension was heated under reflux, and under a nitrogen atmosphere for 5 h. The mixture was cooled, water was added dropwise, and the solids were removed by filtration through dicalite. The filter was washed with hot tetrahydrofuran and the combined filtrate and washings were evaporated to give 16β-hydroxy-17α-methylamino-5α-androstan-3-one ethylene acetal as a colourless residue (5.0 g.).

A solution of the residue (5.0 g) in aqueous acetic acid (10%; 100 ml) was heated on a water bath for 45 min., then water and charcoal were added. The mixture was stirred briefly then filtered. Sodium hydroxide (4 N) was added to the ice-cooled solution and the mixture was extracted with methylene dichloride. The extracts were washed with water, dried (MgSO₄) and evaporated to give a solid residue (3.1 g), which was dissolved in methylene dichloride (30 ml). A solution of maleic acid (1.1 g) in acetone (20 ml) was added and the solvent was evaporated giving a gum (2.9 g), which crystallised from methylene dichloride-acetone to give 16β-hydroxy-17α-methylamino-5α-androstan-3-one maleate (2.2 g). A second recrystallisation from methylene dichloride-acetone gave an analytical sample, m.p. 194°–203° C., $[\alpha]_D^{DMSO}+12°$ (C 2.1).

A sample of the maleate was dissolved in water, sodium hydroxide (2 N) was added, and the solution was extracted with methylene dichloride. The extract was washed with water, dried (MgSO₄), and evaporated and the residue was crystallised from methylene dichloride-ether to give 16β-hydroxy-17α-methylamino-5α-androstan-3-one as prisms, m.p. 167°–174° C., $[\alpha]_D-2°$ (C 0.9).

EXAMPLE III

17β-Methylamino-5α-androstane-3β,16α-diol 3-acetate

3β,16α-Dihydroxy-5α-androstan-17-one diacetate (18.8 g) was dissolved in a solution of methylamine in ethanol (33%; 188 ml) and the solution was stirred for 45 min. during which time a colourless solid precipitated. Sodium borohydride (10 g) was added portionwise to the stirred suspension, while keeping the temperature below 26° C. After 1½ h. water was added and the product was filtered off and washed with water. The crude material was dissolved in methylene dichloride and the solution was washed with water, dried (MgSO₄), evaporated, and the residue (16.2 g) was crystallised from ether to give 17β-methylamino-5α-androstane-3β,16α-diol 3-acetate (12.2 g) as prisms, m.p. 197°–199° C., $[\alpha]_D-18°$ (C 1.0).

EXAMPLE IV (a) 17β-Methylamino-5α-androstane-3β,16α-diol

Hydrolysis of 17β-methylamino-5α-androstane-3β,16α-diol 3-acetate (4.9 g) with aqueous sodium hydroxide (4 N) and ethanol and crystallisation of the product from isopropanol gave 17β-methylamino-5α-androstane-3β,16α-diol (3.0 g) as needles, m.p. 262°–263° C., $[\alpha]_D^{EtOH}-9.0°$ (C 1.0).

(b) 17β-Methylamino-5α-androstane-3β,16α-diol maleate

In a similar way as described in Example (IIb) 17β-methylamino-5α-androstane-3β,16α-diol was converted into 17β-methylamino-5α-androstane-3β,16α-diol maleate. The product was crystallised from ether-ethanol to give an analytical sample, m.p. 124°–126° C., $[\alpha]_D^{MeOH}-4.0°$ (C 0.6).

EXAMPLE V

17β-Methylamino-16α-tetrahydropyranyloxy-5α-androstan-3β-ol

17β-Methylamino-5α-androstane-3β,16α-diol 3-acetate (10 g) was converted to the hydrochloride. Dihydropyran (10 ml) and p-toluenesulphonic acid (1.0 g) were added to a stirred solution of the hydrochloride (10 g) in chloroform (100 ml) giving a colourless suspension, which was stirred at room temperature for 35 min. to give a solution. After a further 1 h., the solvent was evaporated to give a solid residue (10.5 g), which was dissolved in ethanol (105 ml). The solution was heated under reflux for 2 h. with sodiumhydroxide solution (10.5 ml; 4 N) cooled, and water was added to give a solid, which was filtered off and dried (8.5 g).

Crystallisation of the product three times from ether gave pure 17β-methylamino-16α-tetrahydropyranyloxy-5α-androstan-3β-ol (6.6 g) as a mixture of diastereo-isomers, m.p. 105°–120° C.

EXAMPLE VI (a) 16α-Hydroxy-17β-methylamino-5α-androstan-3-one

A solution of 17β-methylamino-16α-tetrahydropyranyloxy-5α-androstan-3β-ol (8.5 g) in methylene dichloride (175 ml) was added to a stirred suspension of pyridinium chlorochromate (25.5 g) and sodium acetate (5.1 g) in methylene dichloride (175 ml) and the mixture was stirred at room temperature for 2 h. Water was added, followed by aqueous sodium hydroxide (4 N) and the methylene dichloride layer was washed with further portions of sodium hydroxide solution and water, dried (MgSO$_4$) and evaporated to give a gum (6.7 g). A solution of the product in glacial acetic acid (100 ml) and hydrochloric acid (2N; 10 ml) was heated on a water bath for 45 min., then set aside for 1 h. Aqueous sodium hydroxide (4 N) was added with ice-cooling and the mixture was extracted with chloroform. The chloroform extracts were washed with water, dried (MgSO$_4$) and evaporated under reduced pressure to give a solid residue (4.2 g) which was triturated with ether to give 16α-hydroxy-17β-methylamino-5α-androstan-3-one (3.4 g). Crystallisation from methylene dichloride-ether gave an analytical sample, m.p. 170°–174° C., $[\alpha]_D+4°$ (C 0.7).

(b) 16α-Hydroxy-17β-methylamino-5α-androstan-3-one maleate

A sample of 16α-hydroxy-17β-methylamino-5α-androstan-3-one was converted to the maleate, which was crystallised from methylene dichloride-acetone to give pure 16α-hydroxy-17β-methylamino-5α-androstan-3-one maleate as prisms, m.p. 204°–207° C., $[\alpha]_D{}^{DMSO}+8°$ (C 1.0).

EXAMPLE VII (a) 17β-Methylacetamido-5α-androstane-3,16-dione

A solution of 17β-methylamino-5α-androstane-3β,16α-diol 3-acetate (6 g) in pyridine (12 ml) and acetic anhydride (6 ml) was heated on a water bath for 2 h., then cooled in an ice-water bath, and water was added to precipitate the product as a pale yellow crystalline solid which was filtered off and washed with water. The product was dissolved in methylene dichloride and the solution was washed with aqueous hydrochloric acid (2 N), water, dried (MgSO$_4$) and evaporated to give a solid (6.8 g), which was crystallised from ether giving 17β-methylacetamido-5α-androstane-3β,16α-diol diacetate as a mixture of rotamers (6.3 g).

A solution of the triacetate (6 g) in ethanol (120 ml) and aqueous sodium hydroxide (2 N; 12 ml) was heated under reflux for 2 h., the solution cooled and water added to precipitate the product which was filtered off, washed with water and dried in vacuo to give crude 17β-methylacetamido-5α-androstane-3β,16α-diol (4.25 g).

Kiliani reagent (11.9 ml) was added dropwise to a stirred solution of the N-acetyl compound (3.46 g) in acetic acid (35 ml) and the solution was stirred at room temperature for 1½ h. Water and aqueous brine were added and the mixture was extracted with methylene dichloride. The extracts were washed with water, saturated potassium hydrogen carbonate solution and water, dried (MgSO$_4$) and evaporated to give a gum (2.7 g). Crystallisation of the product twice from ether yielded 17β-methylacetamido-5α-androstane-3,16-dione as prisms (2.1 g), m.p. 185°–198° C. (decomp.), $[\alpha]_D-207°$ (C 0.9).

(b) 16β-Hydroxy-17β-methylamino-5α-androstan-3-one

17β-Methylacetamido-5α-androstane-3,16-dione (2.1 g), triethyl orthoformate (1.05 ml), methanol (10.5 ml) and p-toluenesulphonic acid (0.05 g) were stirred at room temperature for 45 min. Pyridine (0.06 ml) and water were added to precipitate 17β-methylacetamido-5α-androstane-3,16-dione 3-dimethyl acetal, which was filtered off and dried in vacuo (2.18 g).

A solution of the product (2.0 g) in methanol was reduced with sodium borohydride to give 16β-hydroxy-17β-methylacetamido-5α-androstan-3-one dimethyl acetal (1.84 g). Hydrolysis of the product (1.5 g) with aqueous potassium hydroxide solution (10 N) in ethanol gave 16β-hydroxy-17β-methylamino-5α-androstan-3-one dimethyl acetal (1.2 g). Hydrolysis with aqueous acetic acid (10%) then gave 16β-hydroxy-17β-methylamino-5α-androstan-3-one (1.2 g). Crystallisation from ether yielded an analytical sample m.p. 156°–160° C., $[\alpha]_D+31°$ (C 0.7).

(b) 16β-Hydroxy-17β-methylamino-5α-androstan-3-one maleate

A sample was converted to the maleate which was crystallised from acetone to give 16β-hydroxy-17β-methylamino-5α-androstan-3-one maleate as prisms, m.p. >300° C. (decomp.), $[\alpha]_D{}^{DMSO}+31°$ (C 0.9).

EXAMPLE VIII

17β-Methylamino-5α-androstane-3β,16α-diol 3-acetate hydrochloride

A cold (0° C.) solution of hydrogen chloride (2 g) in methanol (10 ml) was added with stirring to a solution of 17β-methylamino-5α-androstane-3β,16α-diol 3-acetate (16 g) in methanol (16 ml) and chloroform (48 ml) at 0° C. Ether (300 ml) was added to precipitate 17β-methylamino-5α-androstane-3β,16α-diol 3-acetate hydrochloride as prisms (16 g), m.p. >270° C. (decomp.), $[\alpha]_D+113°$ (C 1.04 in MeOH).

EXAMPLE IX (a) 17β-(N-acetyl-methylamino)-5α-androstane-3β,16β-diol

A solution of 17β-methylamino-5α-androstane-3β,16α-diol 3-acetate (15 g) in pyridine (30 ml and acetic anhydride (15 ml) was heated on a water bath for 2 h. The solution was cooled in an ice-water bath and water was added to precipitate the product as a pale yellow crystalline solid, which was filtered off and washed with water. The product was dissolved in dichloromethane and the solution was washed with aqueous hydrochloric acid (2 N), water, dried (MgSO$_4$) and evaporated to give a solid (14.02 g), which was crystallised from ether to give 17β-(N-acetyl-methylamino)-5α-androstane-3β,16α-diol diacetate as a mixture of rotamers (16.7 g).

A solution of the triacetate (16.5 g) in ethanol (330 ml) and aqueous sodium hydroxide (33 ml; 2 N) was heated under reflux for 2 h. The solution was cooled and water was added to precipitate the product, which was filtered off, washed with water and dried in vacuo to give crude 17β-(N-acetyl-methylamino)-5α-androstane-3β,16α-diol as a mixture of rotamers (13.6 g).

Kiliani reagent (49.5 ml) was added dropwise to a stirred solution of the N-acetyl compound (13.5 g) in acetic acid (135 ml) and the solution was stirred at room temperature for 1½ h. Water and brine were added and the mixture was extracted with dichloromethane. The extracts were washed with water, saturated potassium hydrogen carbonate solution and water, dried (MgSO$_4$) and evaporated to give a gum (10.28 g).

Crystallisation of the product twice from ether yielded 17β-(N-acetyl-methylamino)-5α-androstane-3,16-dione as prisms (8.30 g), m.p. 185°-198° C. (decomp.), $[\alpha]_D$ −207° (C 0.9 in CHCl$_3$).

A stirred suspension of the dione (8.2 g) in methanol (123 ml) was cooled in an ice-water bath and sodium borohydride (5.5 g) was added portionwise over 30 min. After 2 h., water was added to precipitate the product as a colourless solid, which was filtered off, washed with water and dried. Crystallisation three times from ethanol gave 17β-(N-acetyl-methylamino)-5α-androstane-3β,16β-diol (4.82 g).

(b) 17β-Methylamino-5α-androstane-3β,16β-diol

Potassium hydroxide (4.8 ml; 10 N) was added to a stirred suspension of 17β-(N-acetyl-methylamino)-5α-androstane-3β,16β-diol (4.8 g) in ethanol (96 ml) and the stirred mixture was heated under reflux for 2 h. A clear solution was obtained after 5 min., and a solid product precipitated after 30 min. The mixture was cooled, water was added, followed by brine and the product was filtered off and washed with water. Crystallisation from aqueous ethanol gave 17β-methylamino-5α-androstane-3β,16β-diol as prisms (3.5 g), m.p. 241°-253° C.

EXAMPLE X

17β-Methylamino-5α-androstane-3β,16β-diol (Z)-2-butenedioate (1:1) (salt)

A solution of maleic acid (1.1 g) in ethanol (30 ml) was added to a solution of 17β-methylamino-5α-androstane-3β,16β-diol (3.05 g) in methanol (600 ml) and the solution was concentrated, treated with charcoal, and filtered. The filtrate was evaporated to give a froth (3.9 g), which crystallised from acetone to give 17β-methylamino-5α-androstane-3β,16β-diol (Z)-2-butenedioate (1:1) (salt) (3.19 g), m.p. 126°-129° C. and 184°-187° C., $[\alpha]_D$ +21.2° (c 1.05 in MeOH).

EXAMPLE XI

17β-Amino-5α-androstane-3β,16α-diol

A solution of diborane in tetrahydrofurane (257 ml; 1 M) was added dropwise to a stirred solution of 3β,16α-bis(acetyloxy)-5α-androstan-17-one oxime acetate (11.7 g) in tetrahydrofuran (257 ml) at 0° C. under a nitrogen atmosphere. The solution was set aside at room temperature overnight, then water (35 ml) was carefully added to the cooled (0° C.), stirred solution. Tetrahydrofuran was distilled off and replaced with ethanol (400 ml) and sodium hydroxide solution (12 ml; 4 N), and the solution was heated under reflux for 3 h. The solution was concentrated and cooled; water (100 ml) and concentrated hydrochloric acid (12 ml) were added and the solution was heated on a water bath for 1 h. Aqueous sodium hydroxide (2 N) was then added to the cooled solution to precipitate the product, which was filtered off, washed with water and dried in vacuo to give 17β-amino-5α-androstane-3β,16α-diol (6.7 g), m.p. 234°-237° C. (decomp.), $[\alpha]_D$ −3.8° (c 1.1 in MeOH).

EXAMPLE XII

17β-Amino-5α-androstane-3β,16α-diol (Z)-2-butenedioate (1:1) (salt)

A solution of maleic acid (2.5 g) in ethanol (25 ml) was added to a solution of 17β-amino-5α-androstane-3β,16α-diol (6.6 g) in ethanol (300 ml). Evaporation of the solvent and crystallisation of the residue from methanol-ethylacetate gave 17β-amino-5α-androstane-3β,16α-diol (Z)-2-butenedioate (1:1) (salt) as prisms (3.1 g), m.p. 193°-197° C., $[\alpha]_D$ −9° (c, 0.9 in MeOH).

EXAMPLE XIII

17α-Amino-5α-androstane-3β,16α-diol 3-acetate

A solution of 3β,16α-dihydroxy-5α-androstan-17-one diacetate (11.0 g) in ethanol/ammonia (50%; 555 ml) was stirred at room temperature for 25 min. Sodium borohydride (5.5 g) was added and the solution was stirred for a further 25 min., then concentrated. Water was added and the precipitated product was extracted with methylene dichloride. The extracts were washed with water, dried (MgSO$_4$), evaporated and the solid residue was converted to a mixture of hydrochlorides from which the water-insoluble 17α-amino-5α-androstane-3β,16α-diol 3-acetate hydrochloride was easily isolated as prisms (4.0 g), m.p. 220° C. (sweating), $[\alpha]_D^{DMSO}$ −31° (C 1.3). Sodium hydroxide (2 N) was added to the aqueous filtrate to precipitate a gelatinous solid, which was extracted with methylene dichloride. The extracts were washed with water, dried (MgSO$_4$) and evaporated to give impure 17β-amino-5α-androstane-3β,16α-diol 3-acetate.

A sample of the 17α-amino-3β,16α-diol 3-acetate hydrochloride was treated with saturated potassium hydrogen carbonate to give the free base, which on crystallisation from methylene dichloride-ether gave pure 17α-amino-5α-androstane-3β,16α-diol 3-acetate as prisms, m.p. 192°-193° C., $[\alpha]_D^{DMSO}$ −18° (C 0.8).

EXAMPLE XIV

17α-Amino-5α-andorstane-3β,16α-diol

Hydrolysis of 17α-amino-5α-androstane-3β,16α-diol 3-acetate (4.8 g) with sodium hydroxide (4 N) and ethanol at reflux temperature gave 17α-amino-5α-androstane-3β,16α-diol (3.4 g). Crystallisation from ethanol yielded an analytical sample, m.p. 220°-225° C.

EXAMPLE XV (a)

16α,17α-(N-ethoxycarbonylimine)-5α-androstan-3β-ol

A solution of triethylamine (20 ml) in dichloromethane (278 ml) was added dropwise over 4 h. to a stirred solution of 5α-androst-16-en-3β-ol (15.26 g) and p-nitrobenzenesulphonoxyurethane (40.4 g) in dichloromethane (278 ml), then the solution was set aside at room temperature overnight. The solution was washed with water (3×300 ml), dried (MgSO$_4$) and the solvent was removed in vacuo yielding a gum (38.2 g). Crystallisation (twice) from ether gave 16α,17α-(N-ethoxycarbonylimine)-5α-androstan-3β-ol as prisms (6.7 g). Chromatography of the mother liquor on silica gel (180 g)

gave a further quantity of pure product (2.94 g). Recrystallisation of a sample from acetone gave colourless needles, m.p. 195°–197° C., $[\alpha]_D$ +24° (c 0.86 in CHCl$_3$).

(b) 16α,17α-imino-5α-androstan-3β-ol

A solution of 16α,17α-(N-ethoxycarbonylimino)-5α-androstan-3β-ol (8.45 g) in potassium hydroxide in ethanol (845 ml; 1 N) was heated under reflux for 1½ h., then concentrated to half volume in vacuo. Water and brine were added and the product was extracted into ether. The organic layer was washed with brine, dried (MgSO$_4$) and evaporated to give a gum (6.64 g). Crystallisation from ether gave 16α,17α-imino-5α-andorstan-3β-ol (4.34 g), m.p. 169°–171° C., $[\alpha]_D$ +15° (c 0.81 in CHCl$_3$).

(c) 16α,17α-(N-acetylimino)-5α-androstan-3β-ol acetate

Acetic anhydride (6 ml) was added to a solution of 16α,17α-imino-5α-androstan-3β-ol (3.0 g) in pyridine (15 ml) and the solution was set aside overnight at room temperature. Water was added to the cooled, stirred solution to precipitate the acetylated product as a colourless solid, which was filtered off and dissolved in dichloromethane. The organic solution was washed with water, saturated potassium bicarbonate solution and water, dried (MgSO$_4$), and evaporated to give a gum (3.6 g). Crystallisation from aqueous methanol gave 16α,17α-(N-acetylimino)-5α-androstan-3β-ol acetate (3.3 g), m.p. 150°–152° C., $[\alpha]_D$ +10° (c 0.85 in CHCl$_3$).

(d) 16β,17β-Dihydro-2'-methyl-5α-androstano[17,16-d]oxazol-3β-ol acetate

A solution of 16α,17α-(N-acetylimino)-5α-androstan-3β-ol acetate (3.2 g) and sodium iodide (12.8 g) in acetone (256 ml) was heated under reflux for 10 h. The solution was concentrated to low volume and cooled, water was added and the yellow precipitate was filtered off, washed with water and dried (wt. 2.6 g). A solution of the product in dichloromethane, was treated with charcoal to remove colour, then it was filtered and the filtrate was evaporated to give a colourless residue (2.4 g). Crystalllisation from ether yield 16β,17β-dihydro-2'-methyl-5α-androstano[17,16-d]oxazol-3β-ol acetate (1.8 g), m.p. 199°–200° C. $[\alpha]_D$ −32° (c 0.88 in CHCl$_3$).

(e) 17α-Amino-5α-androstane-3β,16α-diol and its hydrobromide

A solution of 16β,17β-dihydro-2'-methyl-5α-androstano-[17,16-d]oxazol-3β-ol acetate (1.7 g) in sulphuric acid (30 ml; 5 N) was heated under reflux for 18 h., then cooled and water was added to precipitate a yellow gum which was filtered off. The filtrate was made alkaline with sodium hydroxide solution (4 N), while cooling, and the mixture was extracted into ether. The ether extracts were washed with water, dried (MgSO$_4$) and evaporated to give a gum (0.53 g). Crystallisation from ether gave 17α-amino-5α-androstane-3β,16α-diol (0.4 g), m.p. 220°–225° C.

Reaction with hydrogen bromide in methanol/chloroform and ether-precipitation gave the hydrobromide salt, m.p. <260° C. (decomp.).

EXAMPLE XVI (a) 17β-Methylamino-androst-5-ene-3β,16α-diol 3 acetate

3β,16α-bis(Acetyloxy)-androst-5-en-17-one (2.04 g) was dissolved in methylamine solution (20.4 ml; 33% in methanol) and the solution was stirred at room temperature for 20 min. during which time the 17,17-methylimine crystallised out. Sodium borohydride (1.02 g) was added portionwise to the stirred suspension, keeping the temperature below 25° C. After 1½ h., the excess methylamine was removed under reduced pressure, water (200 ml) was added, and the mixture was extracted with dichloromethane. The extracts were washed with water, dried (Na$_2$SO$_4$) and evaporated to give a white froth (2.07 g), crystallisation of which from dichloromethane-ether afforded pure 17β-methylamino-androst-5-ene-3β,16α-diol 3-acetate as needles, (1.74 g; 91.6%) m.p. 192°–194° C., $[\alpha]_D$ −79.4° (c 0.75 in CHCl$_3$).

(b) 17β-Methylamino-androst-5-ene-3β,16α-diol

Sodium hydroxide solution (1.63 ml; 4 N) was added to a solution of 17β-methylamino-androst-5-ene-3β,16α-diol 3-acetate (1.63 g) in ethanol (32.6 ml) and the resultant solution was refluxed for 1 h. Water (350 ml) was added and the precipitated crude product was filtered off and washed with water. The product was dissolved in a mixture of dichloromethane-methanol ($\approx$1:1) and treated with charcoal. After filtration through dicalite, the filtrates were evaporated to dryness and the resultant offwhite solid was crystallised from methanol-dichloromethane-ether to give pure 17β-methylamino-androst-5-ene-3β,16α-diol as needles (1.25 g; 86.8%), m.p. 241°–246° C. (decomp.), $[\alpha]_D$ −100.2° (c 0.93 in pyridine).

EXAMPLE XVII

17β-Methylamino-androst-5-ene-3β,16α-diol (Z)-2-butenedioate

17β-Methylamino-androst-5-ene-3β,16α-diol (1.15 g) was suspended in methanol (23 ml) and a solution of maleic acid (0.42 g) in methanol (4.2 ml) was added. The resulting solution was treated with charcoal, filtered and the filtrates were evaporated under reduced pressure. Crystallisation of the residue from acetone afforded pure 17β-methylamino-androst-5-ene-3β,16α-diol (Z)-2-butenedioate (1:1) (salt) as an amorphous solid (1.42 g; 90.4%), m.p. 135° C.-(softens)-145° C., $[\alpha]_D$ −55.4° (c 0.83 in D.M.S.O.).

EXAMPLE XVIII (a) 5α,6β-Dichloro-17β-methylamino-5α-androstane-3β,16α-diol 3-acetate 3β,16α-bis(Acetyloxy)-5α-androstan-17-one (15 g) was added to a stirred solution of methylamine in ethanol (150 ml; 35% m/m) at 0° C. After 3 min., complete dissolution had taken place, while after 9 min., the 17,17-methylimino intermediate precipitated. After 35 min., sodium borohydride (7.5 g) was added portionwise with stirring to the cooled (0° C.) suspension and stirring was continued for 1½ h. Water was added to precipitate the product, which was filtered off and washed with water. The product was dissolved in chloroform, the solution was dried (MgSO$_4$) and evaporated, and the solid residue was crystallised from dichloromethane-ether to give 5α,6β-dichloro-17β-methylamino-5α-androstane-3β,16α-diol 3-acetate as prisms (13.0 g), m.p. 208° C. (decomp.), $[\alpha]_D -68°$ (c 1.2 in CHCl$_3$).

(b)

5α,6β-Dichloro-17β-methylamino-androstane-3β,16α-diol

A stirred suspension of 5α,6β-dichloro-17β-methylamino-5α-androstane-3β,16α-diol 3-acetate (13 g) in methanol (105 ml) and aqueous potassium hydroxide solution (3.9 ml; 10 N) was heated under reflux for 1 hr., cooled and water was added to precipitate the product as a white solid, which was filtered off, and washed with water (wt. 11 g). Recrystallisation of a sample from methanol gave 5α,6β-dichloro-17β-methylamino-5α-androstane-3β,16α-diol as prisms, m.p. 194°–195° C. (decomp.).

(c)

5α,6β-Dichloro-17β-methylamino-5α-androstane-3β,16α-diol hydrochloride

Hydrogen chloride gas has passed through a solution of 5α,6β-dichloro-17β-methylamino-5α-androstane-3β,16α-diol (7.2 g) in methanol (15 ml) and chloroform (72 ml), giving a colourless precipitate. Evaporation of the solvent gave a colourless residue which was heated with acetone, filtered, and dried in vacuo to give 5α,6β-dichloro-17β-methylamino-5α-androstane-3β,16α-diol hydrochloride as prisms (7.5 g), m.p.>210° C. (decomp.), $[\alpha]_D -57.1°$ (c 1.1 in EtOH).

(d) 16α-Hydroxy-17β-methylamino-androst-4-en-3-one

Lithium chloride (3.7 g) was added to N,N-dimethyl formamide (74 ml) heated to 100° C. in a silicon fluid bath and under a dry nitrogen atmosphere. 5α,6β-Dichloro-17β-methylamino-5α-androstane-3β,16α-diol hydrochloride (7.4 g) was added and the solution was heated at 100°–115° C. for 3½ h. under a nitrogen atmosphere. The solution was cooled and sodium hydroxide solution (4 N) was added to precipitate the product as a fine, off-white solid, which was filtered off and washed with water. The product was dissolved in chloroform-methanol and the solution was washed to neutrality with water, dried (MgSO$_4$) and evaporated to give a cream coloured solid (4.38 g). Crystallisation from acetone gave 16α-hydroxy-17β-methylamino-androst-4-en-3-one as prisms (2.47 g), m.p. 198°–201° C. (decomp.), $[\alpha]_D +78°$ (c 1.0 in CHCl$_3$).

EXAMPLE XIX

16α-Hydroxy-17β-methylamino-androst-4-en-3-one (Z)-2-butenedioate (1:1) (salt)

A solution of maleic acid (0.73 g) in ethanol (15 ml) was added to a solution of 16α-hyroxy-17β-methylamino-androst-4-en-3-one (2 g) in dichloromethane (15 ml) and ethanol (15 ml). Evaporation of the solvent gave a solid residue which was crystallised from dichloromethane-acetone to give 16α-hydroxy-17β-methylamino-androst-4-en-3-one (Z)-2-butenedioate as prisms (2.65 g), m.p. 193° C. (decomp.), $[\alpha]_D +114°$ (c 0.88 in EtOH).

EXAMPLE XX (a)

16α-Hydroxy-17β-(N-trifluoroacetyl-methylamino)-androst-4-en-3-one

16α-Hydroxy-17β-methylamino-androst-4-en-3-one (3.5 g) was added to a cold (0° C.) solution of trifluoroacetic anhydride (4 ml) in pyridine (21 ml). The solution was stirred at room temperature for 1½ h., cooled, then water was added to precipitate the product as a yellow solid. Crystallisation from ether-n-hexane gave 16α-hydroxy-17β-(N-trifluoroacetylmethylamino)-androst-4-en-3-one as yellow prisms (1.9 g), m.p. 217°–220° C., $[\alpha]_D +5.7°$ (c 1.06 in CHCl$_3$).

(b)

16α-Acetyloxy-17β-(N-trifluoroacetyl-methylamino)-androst-4-en-3-one

A solution of 16α-hydroxy-17η-(N-trifluoroacetyl-methylamino)-androst-4-en-3-one (1.8 g) in pyridine (9 ml) and acetic anhydride (3.6 ml) was set aside at room temperature for 3 h. Cold water (0° C.) was added to precipitate the product, a pale yellow solid, which was filtered off and washed with water; the solution was dried (MgSO$_4$) and evaporated to give a yellow gum (1.98 g). Crystallisation from dichloromethane-ethanol gave 16α-acetyloxy-17β-(N-trifluoroacetyl-methylamino)-androst-4-en-3-one as prisms (1.4 g), m.p. 173°–174° C. $[\alpha]_D +10.9°$ (c 0.9 in CHCl$_3$).

(c)

16α-Hydroxy-17β-methylamino-androsta-1,4-dien-3-one (Z)-2-butenedioate (1:1) (salt)

A solution of 16α-acetyloxy-17β-(N-trifluoroacetyl-methylamino)-androst-4-en-3-one (1.88 g) and diphenylselenic anhydride (1.7 g) in chlorobenzene (39 ml) was heated under reflux for 1 h. The solution was cooled, toluene was added and the solution was filtered through a column (7.5 cm×2.5 cm) of silica gel (0.063–0.2 mm). Elution with toluene removed diphenylselenide. Elution with ether yielded a fraction which was evaporated to dryness to give 16α-acetyloxy-17β-(N-trifluoroacetyl-methylamino)-androsta-1,4-dien-3-one as a yellow gum (1.52 g). A solution of the product in ethanol (40 ml) and aqueous sodium hydroxide solution (3 ml; 4 N) was heated under reflux for 1.5 h.; the solution was concentrated and cooled, then water was added to precipitate an off-white solid, which was filtered off, washed with water and dried in vacuo to give 16α-hydroxy-17β-methylamino-androsta-1,4-dien-3-one (1 g). The product was dissolved in ethanol (20 ml), a solution of maleic acid (0.37 g) in ethanol (10 ml) was added and the resulting solution was treated with charcoal, filtered and evaporated to give a pale yellow gum (1.44 g). Crystallisation from acetone gave 16α-hydroxy-17β-methylamino-androsta-1,4-dien-3-one (Z)-2-butenedioate (1:1) (salt) as colourless prisms (0.88 g), m.p. 184°–191° C. (decomp.), $[\alpha]_D +14.2°$ (c 0.88 in ETOH).

EXAMPLE XXI (a) 17β-Methylamino-oestra-1,3,5(10)-triene-3,16α-diol and its hydrochloride 3,16α-Dihydroxy-oestra-1,3,5(10)-trien-17-one diacetate (32.4 g) was stirred with methylamine solution (324 ml; 33% in EtCH) for 20 min. Sodium borohydride (16.2 g) was added portionwise to the stirred solution, keeping the temperature at <25° C. After 1½ h., the methylamine was removed under reduced pressure and the residue was acidified with hydrochloric acid (5 N). The mixture was rebasified with saturated potassium bicarbonate solution to give crude product, which was filtered off, washed with water and suspended in methanol. The suspension was boiled for 5 min., cooled and filtered to give pure 17β-methylamino-oestra-1,3,5(10)-triene-3,16α-diol as an amorphous solid (23.5 g; 89%), m.p. 242°–246° C. (decomp.), $[\alpha]_D$ +48° (c 1.0 in D.M.S.O.).

The hydrochloride was obtained in the usual manner as prisms (methanol-ether) m.p. >300° C. (decomp.), $[\alpha]_D$ +45° (c 0.9 in D.M.S.O.).

Action of acetylchloride on the hydrochloride obtained above in acetic acid afforded the 3,16α-diacetate.

(b)
dl-17β-Methylamino-oestra-1,3,5(10)triene-3,16α-diol and its hydrochloride

By starting from dl-3,16α-dihydroxy-oestra-1,3,5(10)-trien-17-one diacetate the procedure of Example XXI (a) gave dl-17β-methylamino-oestra-1,3,5(10)-triene-3,16α-diol and its hydrochloride.

(c)
ent-17β-Methylamino-oestra-1,3,5(10)-triene-3,16α-diol and its hydrochloride In a similar way as described in Example XII (a) the title compounds were prepared starting from ent-3,16α-dihydroxy-oestra-1,3,5(10)-trien-17-one. ent-17β-Methylamino-oestra-1,3,5-(10)-triene-3,16α-diol has a m.p. of 240°–245° C. (decomp.) and $[\alpha]_D$ −48° (c 1.0 in D.M.S.O.). The hydrochloride melted above 300° C. with decomposition, $[\alpha]_D$ −45° (c 0.9 in D.M.S.O.)

EXAMPLE XXII (a)
17β-Methylacetamido-oestra-1,3,5(10)-triene-3,16α-diol diacetate 17β-Methylamino-oestra-1,3,5(10)-triene-3,16α-diol (13.45 g) was suspended in pyridine (40 ml) and acetic anhydride (20 ml) added. The mixture was heated on a steam bath for 2½ h. (solution obtained after 0.5 h.), cooled to room temperature and water (400 ml) added. The gum obtained was extracted into dichloromethane and the extract washed with water, hydrochloric acid (2 N), water and dried (Na₂SO₄). Evaporation afforded an isomeric mixture 17β-methylacetamido-oestra-1,3,5(10)-triene-3,16α-diol diacetates as a yellow gum (19.1 g, 100%).

(b)
17β-Methylacetamido-oestra-1,3,5(10)-triene-3,16α-diol

17β-Methylacetamido-oestra-1,3,5(10)-triene-3,16α-diol diacetate (19.7 g) was dissolved in ethanol (394 ml) and sodium hydroxide (50.9 ml; 2 N) was added. The resulting solution was refluxed for 1 h., cooled to room temperature and water (4 l) was added. The mixture was acidified with hydrochloric acid (2 N) and the precipitated product was filtered off and washed with water. Crystallisation from methanol-ether gave an isomeric mixture of 17β-methylacetamido-oestra-1,3,5(10)-triene-3,16α-diols (13.1 g; 83%).

(c)
17β-Methylacetamido-oestra-1,3,5(10)-triene-3,16α-diol 3-benzoate

17β-Methylacetamido-oestra-1,3,5(10)-triene-3,16α-diol (13.1 g) was dissolved in aqueous sodium hydroxide solution (260 ml; 2 N), acetone (260 ml) and water (260 ml). Benzoyl chloride (6.5 ml) was added and the mixture stirred vigorously for 10 min.; a further 6.5 ml of benzoyl chloride was added and the mixture was stirred vigorously for a further 10 min. Water (5 l) was added and the precipitated product was filtered, washed with water and dissolved in dichloromethane. The dichloromethane solution was washed with water, dried (Na₂SO₄) and evaporated to give a white froth (6.8 g), which was crystallised from dichloromethane-ether-light petroleum to give impure product (6.0 g). Acidification of the aqueous mother liquors provided unreacted starting material (7.8 g), which was treated as above to give a further quantity of impure product (2.3 g). Recrystallisation of the combined products from dichloromethane-ether afforded an isomeric mixture of 17β-methylacetamido-oestra-1,3,5(10)-triene-3,16α-diol 3-benzoates (4.68 g; 27%).

(d)
3-Hydroxy-17β-methylacetamido-oestra-1,3,5(10)-trien-16-one benzoate.

17β-Methylacetamido-oestra-1,3,5(10)-triene-3,16α-diol 3-benzoate (4.6 g) was dissolved in glacial acetic acid (46 ml) and Kiliani reagent (6.82 ml, 1.1 g atoms) added. The mixture was stirred at room temperature for 45 min., (product precipitated after 15 min.) and water (500 ml) was added. The product was filtered off, washed with water and dissolved in dichloromethane. The dichloromethane solution was washed with water, dried (Na₂SO₄) and evaporated to give a yellow gum (6.4 g). Crystallisation from dichloromethane afforded impure material (3.69 g) which was redissolved in dichloromethane and filtered through an alumina column (100 g). Elution with dichloromethane gave 3-hydroxy-17β-methylacetamido-oestra-1,3,5(10)-trien-16-one benzoate as prisms, (2.88 g; 63%) m.p. 169°–171° C., $[\alpha]_D$ −182° (c 1.0 in CHCl₃).

(e) 17β-Methylamino-oestra-1,3,5(10)-triene-3,16β-diol and its hydrochloride

3-Hydroxy-17β-methylacetamido-oestra-1,3,5(10)-trien-16-one benzoate (2.5 g) was suspended in methanol (25 ml) and cooled to <10° C. Sodium borohydride (3.85 g) was added portionwise to the stirred suspension and the resultant mixture stirred at room temperature for 1 h. Water (250 ml) was added and the precipitated product was filtered off and washed with water. The crude product was dissolved in a mixture of ethanol (50 ml) and aqueous potassium hydroxide solution (5 ml; 10 N) and refluxed for 2 h. Water (500 ml) was added and the mixture was acidified with hydrochloric acid solution (2 N). Addition of aqueous sodium carbonate solution (5%) gave the crude product, which was filtered off, washed with water and suspended in methanol. The suspension was heated and ether was added to give pure 17β-methylamino-oestra-1,3,5(10)-triene-3,16β-diol as an amorphous solid (1.22 g, 72%), m.p. >300° C. (decomp.), $[α]_D$ +45° (c 0.7 in D.M.S.O.).

The hydrochloride was obtained in the usual manner as prisms, m.p. >300° C. (decomp.).

EXAMPLE XXIII (a) 3,16β-bis(Acetyloxy)-oestra-1,3,5(10)-trien-17-one

Lead tetra-acetate (15 g) was added to a solution of oestra-1,3,5(10),16-tetraene-3,17-diol diacetate (10 g) in acetic acid (200 ml) and acetic anhydride (10 ml) and the mixture was shaken at room temperature for 21 h. The solution was evaporated under reduced pressure, toluene was added, and the insoluble lead tetra-acetate was filtered off. The filtrate was washed successively with saturated potassium hydrogen carbonate solution and water, then dried (MgSO₄) and evaporated to give a yellow gum (9.6 g). A solution of the product in toluene was chromatographed on silical gel (250 g). Elution with toluene-ether (9:1) gave a fraction, which was crystallised from ether to give 3,16β-bis-(acetyloxy)-oestra-1,3,5(10)-trien-17-one as prisms (4.6 g), m.p. 144°–148° C.

(b) 17β-Methylamino-oestra-1,3,5(10)-triene-3,16β-diol hydrochloride

A solution of methylamine in ethanol (510 ml; 33% m/m) was cooled to 5° C. in an ice-water bath. The cooling bath was removed and 3,16β-bis(acetyloxy)-oestra-1,3,5(10)-trien-17-one (51 g) was added to the stirred solution. The solution was stirred for 30 min., cooled to 0° C. and sodium borohydride (25.5 g) was added portionwise. The suspension was stirred for 2½ h. at room temperature, then water was added and the stirred mixture was distilled to remove methylamine and the bulk of the ethanol. The residue was acidified with hydrochloric acid (5 N), then solid sodium carbonate was added until the mixture was alkaline. The precipitated product was filtered off, washed with water and dried in vacuo (wt. 25.6 g).

A saturated solution of hydrogen chloride gas in methanol (250 ml) was added to a solution of the product (19 g) in methanol (12 l) and the solution was concentrated to 1 l and cooled to give 17β-methylamino-oestra-1,3,5(10)-triene-3,16β-diol hydrochloride as prisms (11.7 g), m.p. >300° C. (decomp.)

(c) dl-17β-Methylamino-oestra-1,3,5(10)-triene-3,16β-hydrochloride

Repeating the procedure of Example XXIII (a) and (b) on dl-oestra-1,3,5(10),16-tetraene-3,17-diol diacetate gave the title compound.

EXAMPLE XXIV (a) 17β-Methylamino-oestra-1,3,5(10)-triene-3,16α-diol (Z)-2-butenedioate (1:1) (salt)

17β-Methylamino-oestra-1,3,5(10)-triene-3,16α-diol (130 g) was dissolved in methanol (13 l) and the solution was filtered to remove extraneous matter. Maleic acid (50 g) in methanol (800 ml) was added and the resulting solution was concentrated to low volume under reduced pressure. The resulting solution was refluxed with charcoal (18 g), filtered through a dicalite pad and further reduced in volume. The addition of ether afforded pure 17β-methylamino-oestra-1,3,5(10)-triene-3,16α-diol (Z)-2-butenedioate (1:1) (salt) as an amorphous solid (130 g; 72.2%), m.p. 161°–168° C. (decomp.), $[α]_D$ +37.6° (c 0.89 in EtOH).

(b) dl-17β-Methylamino-oestra-1,3,5(10)-triene-3,16α-diol (Z)-2-butenedioate (1:1) (salt)

The same procedure as in Example XXIV (a), when carried out on dl-17β-methylamino-oestra-1,3,5(10)-triene-3,16α-diol, gave the (Z)-2-butenedioate thereof.

(c) ent-17β-Methylamino-oestra-1,3,5(10)-triene-3,16α-diol (Z)-2-butenedioate (1:1) (salt)

The same procedure as in Example XXIV (a), when carried out on ent-17β-methylamino-oestra-1,3,5(10)-triene-3,16α-diol, gave the (Z)-2-butenedioate thereof with m.p. 159°–167° C. (decomp.), $[α]_D$ −37.8° (c 0.9 in EtOH).

EXAMPLE XXV

17β-Methylamino-oestra-1,3,5(10)-triene-3,16β-diol nitrate

A suspension of 17β-methylamino-oestra-1,3,5(10)-triene-3,16β-diol hydrochloride (3.3 g) in ethanol (1,500 ml) and sodium hydroxide (11.0 ml; 2 N) was heated until the steroid was completely dissolved. The solution was concentrated almost to dryness to give a colourless precipitate, which was filtered off, washed with water and dried in vacuo (wt. 3.15 g). The product (2.15 g) was suspended in methanol (40 ml) and nitric acid (13.6 ml; 1 N) and the mixture was again heated until a clear solution was obtained. The solution was concentrated almost to dryness and the precipitated product was filtered off, washed with cold water and crystallised from methanol to give 17β-methylamino-oestra-1,3,5(10)-triene-3,16β-diol nitrate as prisms (1.6 g), m.p. >300° C. (decomp.), $[α]_D$ +76° (c 1.2 in D.M.S.O.).

EXAMPLE XXVI (a) 17β-(N-formyl-N-methylamino)-oestra-1,3,5(10)-triene-3,16α-diol Sodium (1.91 g) was added portionwise to a suspension of 17β-methylamino-oestra-1,3,5(10)-triene-3,16α-diol (6.0 g) in ethylformate (60 ml) and ethanol (30 ml).

The resultant solution was stirred for 2 h., when methanol was added to dissolve the precipitated sodium salt. The solution was acidified with 5 N hydrochloric acid and water (500 ml) was added to precipitate the crude product, which was filtered off and washed with water. Crystallisation from dichloromethane-methanol afforded a mixture of rotameric forms of 17β-(N-formyl-N-methylamino)-oestra-1,3,5(10)-triene-3,16α-diol as prisms (5.41 g; 82.5%), m.p. 272°–276° C., $[\alpha]_D \pm 0°$ (c 1.2 in pyridine).

(b)
17β-Dimethylamino-oestra-1,3,5(10)-triene-3,16α-diol

A suspension of 17β-(N-formyl-N-methylamino)-oestra-1,3,5(10)-triene-3,16α-diol (5.41 g) in tetrahydrofuran (110 ml) was kept at 10° C., while lithium aluminium hydride (5.41 g) was added portionwise. The resultant mixture was refluxed for 5 h., then the excess of lithium aluminium hydride was destroyed by careful addition of water. The mixture was diluted with a 1:1 mixture of tetrahydrofuran-ethylacetate (500 ml) and refluxed for 3 h. The inorganic salts were filtered off and washed with tetrahydrofuran-ethylacetate (500 ml; 1:1) and the filtrate was evaporated to dryness. The resultant crude product was crystallised from dichloromethane-methanol to give pure 17β-dimethylamino-oestra-1,3,5(10)-triene-3,16α-diol as an amorphous solid (3.83 g; 73.9%), m.p. 240°–242° C., $[\alpha]_D +43.4°$ (c 1.33 in pyridine).

(c)
ent-17β-Dimethylamino-oestra-1,3,5(10)-triene-3,16α-diol

The procedure of Examples XXVI (a) and (b) when carried out on ent-17β-methylamino-oestra-1,3,5(10)-triene-3,16α-diol gave ent-17β-dimethylamino-oestra-1,3,5(10)-triene-3,16α-diol, m.p. 238°–241° C., $[\alpha]_D -43.3°$ (c 1.3 in pyridine).

EXAMPLE XXVII (a)
17β-Dimethylamino-oestra-1,3,5(10)-triene-3,16α-diol (Z)-2-butenedioate (1:1) (salt)

17β-Methylamino-oestra-1,3,5(10)-triene-3,16α-diol (1.7 g) was dissolved in dichloromethane (17 ml) and a solution of maleic acid (0.63 g) in methanol (6.3 ml) was added. The resulting solution was evaporated to low volume and acetone was added to give pure 17β-dimethylamino-oestra-1,3,5(10)-triene-3,16α-diol (Z)-2-butenedioate (1:1) (salt) as prisms (1.76 g; 75.5%), m.p. 188°–194° C., $[\alpha]_D +36.1°$ (c 0.98 in MeOH).

(b)
ent-17β-Dimethylamino-oestra-1,3,5(10)-triene-3,16α-diol (Z)-2-butenedioate (1:1) (salt)

The procedure of Example XXVII (a) when carried out on ent-17β-dimethylamino-oestra-1,3,5(10)-triene-3,16α-diol gave the (Z)-2-butenedioate (1:1) thereof, m.p. 187°–193° C., $[\alpha]_D -36°$ (c 1.0 in MeOH).

EXAMPLE XXVIII (a) 17β-Methylamino-oestra-1,3,5(10)-triene-3,16α-diol 3-methylether and its hydrochloride 3,16α-Dihydroxy-oestra-1,3,5(10)-trien-17-one 16-acetate 3-methyl ether (28.2 g) was added to methylamine (282 ml; 33% in ethanol) and the resultant solution stirred at room temperature for 20 min. Sodium borohydride (14.1 g) was added portionwise to the solution keeping the temperature below 25° C. After 1½ h. the methylamine was removed under reduced pressure and water (2 l) was added. The precipitated product was filtered, washed with water, dissolved in methanol and the extraneous matter removed by filtration. The solution was concentrated and ether was added to give 17β-methylamino-oestra-1,3,5(10)-triene-3,16α-diol 3-methylether as needles, (24.1 g; 93%), m.p. >170° (decomp.), $[\alpha]_D +45°$ (c 1.2 in D.M.S.O.).

The hydrochloride was obtained in the usual manner as prisms (MeOH-Et$_2$O), m.p. >280° C. (decomp.), $[\alpha]_D +50°$ (c 1.0 in D.M.S.O.).

(b)
dl-17β-Methylamino-oestra-1,3,5(10)-triene-3,16α-diol 3-methylether and its hydrochloride The procedure of Example XXVII (a) when carried out on dl-3,16α-dihydroxy-oestra-1,3,5(10)-trien-17-one 16-acetate 3-methylether gave the title compound and its hydrochloride.

(c)
ent-17β-Methylamino-oestra-1,3,5(10)-triene-3,16α-diol 3-methylether and its hydrochloride ent-17β-Methylamino-oestra-1,3,5(10)-triene-3,16α-diol 3-methylether with m.p. 164°–166° C. and $[\alpha]_D -55.8°$ (c 1.0 in CHCl$_3$) was obtained by resolution of the dl-3-methylether of Example XXVII (b) using camphor-10-sulphonic acid for making the diastereo-isomeric mixture, which is then fractionally crystallised followed by alkaline hydrolysis. Usual acid addition salt formation afforded the hydrochloride salt, m.p. >285° C. (decomp.), $[\alpha]_D -50.5°$ (c 1.0 in D.M.S.O.).

EXAMPLE XXIX (a)
17β-Methylacetamido-oestra-1,3,5(10)-triene-3,16α-diol 16-acetate 3-methylester 17β-Methylamino-oestra-1,3,5(10)-triene-3,16α-diol 3-methylether (18.9 g) was suspended in pyridine (56.6 ml) and acetic anhydride (28.4 ml) was added. The mixture was heated on the steam bath for 2½ h. (a solution was obtained after 0.5 h.), cooled to room temperature and water (1 l) added. The resultant oil was extracted into dichloromethane and the extracts were washed with hydrochloric acid (2 N) and water, dried (Na$_2$SO$_4$) and evaporated to give a crude mixture of isomeric 17β-methylacetamido-oestra-1,3,5(10)-triene-3,16α-diol 16-acetate 3-methylethers as a yellow gum, (24.0 g; 100%).

(b)
17β-Methylacetamido-oestra-1,3,5(10)-triene-3,16α-diol 3-methylether

17β-Methylacetamido-oestra-1,3,5(10)-triene-3,16α-diol 16-acetate 3-methylether (24.0 g) was dissolved in ethanol (480 ml) and an aqueous solution of sodium hydroxide (31.0 ml; 2 N) was added. The resulting solution was heated under reflux for 1 h. Water (4.5 l) was added to the cooled solution and the precipitated product was filtered and washed with water. Recrystallisation from methanol-ether gave a mixture of isomeric 17β-methyl-acetamido-oestra-1,3,5(10)-triene-3,16α-diol 3-methylethers (17.8 g, 83%).

(c) 3-Hydroxy-17β-methylacetamido-oestra-1,3,5(10)-trien-16-one 3-methylether

17β-Methylacetamido-oestra-1,3,5(10)-triene-3,16α-diol 3-methylether (15.3 g) was dissolved in glacial acetic acid (153 ml) and Kiliani's reagent (56.3 ml; 8 N) was added and the solution stirred at room temperature for 2½ h. Water (1.5 l) was added and the mixture was extracted with dichloromethane. The organic extracts were washed with sodium carbonate solution (5%), water, dried ($Na_2SO_4$) and evaporated to give a yellow gum (15 g), which was dissolved in dichloromethane and filtered through a short column of alumina. Elution with dichloromethane gave a clear gum (8.4 g), which was crystallised from dichloromethane-ether to give pure 3-hydroxy-17β-methylacetamido-oestra-1,3,5(10)-trien-16-one 3-methyl-ether as prisms, (6.8 g; 45%), m.p. 175°–180° C., $[\alpha]_D$ −228° (c 0.8 in $CHCl_3$).

(d) 17β-Methylamino-oestra-1,3,5(10)-triene-3,16β-diol 3-methylether and its hydrochloride Sodium borohydride (2.25 g) was added portionwise to a suspension of 3-hydroxy-17β-methylacetamido-oestra-1,3,5(10)-trien-16-one 3-methylether (6.75 g) in methanol (67.5 ml), keeping the temperature below 10° C. The reaction mixture was stirred at room temperature for 1 h., and water (700 ml) was added. The precipitated product was filtered off and washed with water. Recrystallisation from methanol-ether afforded an isomeric mixture of 17β-methylacetamido-oestra-1,3,5(10)-triene-3,16β-diol 3-methylethers (4.43 g). The product (4.43 g) was dissolved in ethanol (88.6 ml) and aqueous potassium hydroxide solution (4.43 ml; 10 N) was added. The solution was refluxed for 1½ h., water (890 ml) was added and the precipitated product was filtered off and washed with water. Recrystallisation from methanol-ether afforded pure 17β-methylamino-oestra-1,3,5(10)-triene-3,16β-diol 3-methylether as prisms, (3.46 g, 58%), m.p. 180°–182° C., $[\alpha]_D$ +90° (c 0.8 in D.M.S.O.).

The hydrochloride was obtained in the usual manner as prisms ($MeOH$-$Et_2O$), m.p. >300° C. (decomp.).

(e) dl-17β-Methylamino-oestra-1,3,5(10)-triene-3,16β-diol 3-methylester and its hydrochloride The procedure of Examples XXIX (a)–(d) when carried out on dl-17β-methylamino-oestra-1,3,5(10)-triene-3,16α-diol 3-methylether gave the title compounds.

EXAMPLE XXX (a) 17α-Bromo-oestra-1,3,5(10)-triene-3,16β-diol 3-methylether

Oestra-1,3,5(10),16-tetraen-3-ol 3-methylether (26.1 g) was suspended in a mixture of D.M.S.O. (652.5 ml) and water (43.9 ml) at 12° C.; N-bromo-succinimide (20.7 g) was added portionwise and the mixture was stirred for 0.5 h. at <10° C. Water (6 l) was added and the resultant emulsion was broken up by the addition of sodium chloride. The fine solid thus obtained was filtered, washed with water and dissolved in dichloromethane. The dichloromethane solution was washed with sodium meta bisulphite solution, water, dried ($N_2SO_4$) and evaporated to give a dark-brown gum (37.8g), which was redissolved in dichloromethane and filtered through a short silica column to give 17α-bromo-oestra-1,3,5(10)-triene-3,16β-diol 3-methylether as a gum (30.4 g, 86%).

(b) 16β,17β-Expoxy-oestra-1,3,5(10)-trien-3-ol 3-methylether

17α-Bromo-oestra-1,3,5(10)-triene-3,16β-diol 3-methylether (26.1 g) was suspended in a mixture of methanol (300 ml) and aqueous potassium hydroxide solution (30 ml; 10 N) and stirred at reflux for 1.5 h. Water (3 l) was now added and the precipitated product filtered off, washed with water and dissolved in dichloromethane. The dichloromethane solution was washed with water, dried ($Na_2SO_4$) and evaporated to give a brown gum (20.7 g), which was chromatographed on a silica column. Elution with toluene and ether gave the product as a clear gum, which was crystallised from ether-light petroleum to give pure 16β,17β-epoxy-oestra-1,3,5(10)-trien-3-ol 3-methylether as prisms, (16.6 g; 70%) m.p. 111°–113° C., $[\alpha]_D$ +114° (c 1.0 in $CHCl_3$).

(c) 17α-Azido-oestra-1,3,5(10)-triene-3,16β-diol 3-methylether

16β,17β-Epoxy-oestra-1,3,5(10)-trien-3-ol 3-methylether (16.45 g) was dissolved in N,N-dimethylacetamide (175 ml) and a solution of sodium azide (20 g) in water (46 ml) was added. The resulting solution was stirred under reflux for 24 h. Water (1.75 l) was added and the gum obtained was dissolved in dichloromethane. The dichloromethane solution was washed with water, dried ($Na_2SO_4$) and evaporated to give a mixture of 16α-azido-17β-ol and the 17α-azido-16β-ol as a yellow gum (20.2 g). Major impurities were removed by filtration through a column of silica gel, and the resultant mixture (17.43 g) was separated by high pressure liquid chromatography. Elution with toluene-ethyl acetate 2:1 gave 16α-azido-oestra-1,3,5(10)-triene-3,17β-diol 3-methylether as a gum (6.7 g, 35%) and 17α-azido-oestra-1,3,5(10)-triene-3,16β-diol 3-methylether, also as a gum (8.9 g, 47%).

(d) 17α-Amino-oestra-1,3,5(10)-triene-3,16β-diol 3-methylether and its hydrochloride 17α-Azido-oestra-1,3,5(10)-triene-3,16β-diol 3-methylether (8.7 g) in tetrahydrofuran (80 ml) was added dropwise to a cooled suspension of lithium aluminium hydride (2.2 g) in tetrahydrofuran (24 ml). The resultant mixture was stirred under reflux for 1 h., cooled in an ice bath and water was added carefully to destroy the excess of lithium aluminium hydride. The inorganic salts were removed by filtration of the mixture through a dicalite pad, the pad being washed with hot tetrahydrofuran and dichloromethane. The filtrate was evaporated to give a white solid (7.2 g), which was crystallised from dichloromethane-methanol-ether to give 17α-amino-oestra-1,3,5(10)-triene-3,16β-diol 3-methylether as prisms, (5.85 g, 73%), m.p. 173°–176° C., $[\alpha]_D$ +59° (c 1.3 in D.M.S.O.).

The hydrochloride, prepared in the usual manner and crystallised from methylene chloride-methanol-ether had m.p. >260° C. (decomp.), $[\alpha]_D$ +58° (c 0.9 in D.M.S.O.).

(e) ent-17α-Amino-oestra-1,3,5(10)-triene-3,16β-diol 3-methylether and its hydrochloride The procedure of Example XXX (a)–(d) when carried out on ent-oestra-1,3,5(10),16-tetraen-3-ol 3-methylether gave ent-17α-amino-oestra-1,3,5(10)-triene-3,16β-diol 3-methylether, m.p. 171°–175° C.,

[α]$_D$ −58.7 (c 1.3 in D.M.S.O.) and its hydrochloride, m.p. >250° C. (decomp.), [α]$_D$ −58.4 (c 1.0 in D.M.S.O.).

EXAMPLE XXXI (a) 17α-Formamido-oestra-1,3,5(10)-triene-3,16β-diol 3-methylether Sodium (0.28 g) was added to a suspension of 17α-amino-oestra-1,3,5(10)-triene-3,16β-diol 3-methylether (3.66 g) in a mixture of ethylformate (36.6 ml) and ethanol (18.3 ml). After approx. 5 min. the starting material had dissolved and the product started to precipitate. The reaction mixture was stirred at room temperature for 0.5 h., water (500 ml) was added and the product was filtered and washed with water. A solution of the crude product in methanol was filtered and the filtrate was concentrated. Crystallisation from methylene chloride-methanol-ether gave pure 17α-formamido-oestra-1,3,5(10)-triene-3,16β-diol 3-methylether as prisms, (3.58 g, 89.5%) m.p. 231°–233° C., [α]$_D$ +112° (c 0.9 in D.M.S.O.).

(b) 17α-Methylamino-oestra-1,3,5(10)-triene-3,16β-diol 3-methylether and its hydrochloride 17α-Formamido-oestra-1,3,5(10)-triene-3,16β-diol 3-methylether (3.46 g) in tetrahydrofuran (100 ml) was added dropwise to a cooled suspension of lithium aluminium hydride (1.73 g) in tetrahydrofuran (40 ml). The resultant mixture was stirred at reflux temperature for 3 h., cooled in an ice bath and water was added carefully to destroy the excess of lithium aluminium hydride. The inorganic salts were removed by filtration of the mixture through a dicalite paid, the pad being washed with hot tetrahydrofuran and dichloromethane. The filtrate was evaporated to give a clear gum (3.9 g), which was crystallised from dichloro-methane-ether to give 17α-methylamino-oestra-1,3,5(10)-triene-3,16β-diol 3-methylether as prisms, (2.62 g, 79%), m.p. 133°–135° C., [α]$_D$ +42° (c 1.1 in D.M.S.O.).

The hydrochloride, prepared in the usual manner and crystallised as prisms from methylene chloride-methanol-ether had m.p. >270° C. (decomp.), [α]$_D$ +50° (c 0.9 in D.M.S.O.).

(e) ent-17α-Methylamino-oestra-1,3,5(10)-triene-3,16β-diol 3-methylether and its hydrochloride The procedure of Examples XXXI (a) and (b), when carried out on ent-17α-amino-oestra-1,3,5(10)-triene-3,16β-diol 3-methylether gave the title compounds, m.p. 133°–135° C.; [α]$_D$ −41.6° (c 1.1 in D.M.S.O.) and m.p. >260° C. (decomp.), [α]$_D$ −49.7° (c 0.9 in D.M.S.O.), respectively.

EXAMPLE XXXII (a) dl-17β-Methylamino-5α-oestrane-3β,16α-diol (Z)-2-butenedioate In a similar way as described in Examples III and IV starting from dl-3β,16α-dihydroxy-5α-oestran-17-one diacetate, the title compound was prepared.

(b) dl-16α-Hydroxy-17β-methylamino-5α-oestran-3-one (Z)-2-butenedioate

In a similar way as described in Example VI starting from dl-17β-methlyamino-5α-oestrane-3β,16α-diol 3-acetate, the title compound was prepared.

(c) ent-17β-Methylamino-5α-oestrane-3β,16α-diol (Z)-2-butenedioate and the corresponding 3-oxo compound dl-17β-Methylamino-5α-oestrane-3β,16α-diol and the corresponding 3-oxo compound were resolved according to standard procedures by reaction with dibenzoyl tartaric acid, followed by fractional crystallisation and alkaline hydrolysis, and the ent-17β-methylamino-5α-oestrane compounds obtained were converted into the (Z)-2-butenedioate thereof.

EXAMPLE XXXIII (a) 1-Methyl-17β-methylamino-oestra-1,3,5(10)-triene-3,16α-diol The procedure of Example XXI (a) (first part) when carried out on 3,16α-diacetoxy-1-methyl-oestra-1,3,5(10)-trien-17-one gave 1-methyl-17β-methylamino-oestra-1,3,5(10)-triene-3,16α-diol, m.p. 215°–231° C., [α]$_D$+105.7° (c 1.2 in pyridine).

(b) 1-Methyl-17β-methylamino-oestra-1,3,5(10)-triene-3,16α-diol hydrochloride

In a similar way as described infra Example XXIII (b) the compound of Example XXXIII (a) was converted into its hydrochloride, m.p. 280°–291° C. (decomp.), [α]$_D$+115.4° (c 1.13 in methanol).

EXAMPLE XXXIV

17β-Amino-oestra-1,3,5(10)-triene-3,16α-diol citrate (1:1) (salt)

In a similar way as described in Example XIII 3,16α-dihydroxy-oestra-1,3,5(10)-trien-17-one diacetate was converted with a saturated solution of ammonia in ethanol and in the presence of a type 3 Å molecular sieve, followed by sodium borohydride reduction of the intermediate 17-imine, into 17β-amino-oestra-1,3,5(10)-triene-3,16α-diol. Reaction of the latter compound with citric acid gave 17β-amino-oestra-1,3,5(10)-triene-3,16α-diol citrate (1:1) (salt), m.p. >220° C. (decomp.), [α]$_D$+24° (c 0.9 in dimethylsulphoxide).

EXAMPLE XXXV

17β-Methylamino-oestra-1,3,5(10)-triene-3,16α-diol methanesulphonate (1:1) (salt)

In a similar way as described in Example XXIV 17β-methylamino-oestra-1,3,5(10)-triene-3,16α-diol was reacted with methanesulphonic acid to give the title compound, m.p. 268°–270° C.; [α]$_D$+43.8° (c 1.05 in EtOH).

EXAMPLE XXXVI (a) 17β-Ethylamino-oestra-1,3,5(10)-triene-3,16α-diol (Z)-2-butenedioate (1:1) (salt)

In a similar way as described in Example XXI 3,16α-dihydroxy-oestra-1,3,5(10)-trien-17-one diacetate was converted with ethylamine into the intermediate 17-ethylimine, which was reduced with sodium borohydride. Hydrolysis with potassium bicarbonate, followed by treatment with maleic acid gave the title compound, m.p. 147° C. (decomp.), [α]$_D$+32.9° (c 1.07 in dimethylsulphoxide).

(b) 17β-isopropylamino-oestra-1,3,5(10)-3,16α-diol citrate (1:1) (salt)

In a similar way as described in Example XXI 3,16α-dihydroxy-oestra-1,3,5(10)-trien-17-one diacetate was converted with isopropylamine into the intermediate 17-isopropylimine, which was reduced with sodium borohydride. Hydrolysis with potassium bicarbonate, followed by treatment with citric acid gave the title compound, m.p. 206°–209° C. (decomp.), $[\alpha]_D + 41.6°$ (c 1.1 in dimethylsulphoxide).

EXAMPLE XXXVII

17β-Dimethylamino-oestra-1,3,5(10)-triene-3,16α-diol 3-acetate

Acetylation of the compound of Example XXVI (b) with acetylchloride in pyridine gave the corresponding 3-acetate in admixture with a small amount of the 3,16α-diacetate. Isolation by crystallisation gave the title compound, m.p. 173°–175° C., $[\alpha]_D + 31.9°$ (c 0.86 in ethanol).

EXAMPLE XXXVIII (a) 17β-Methylamino-oestra-1,3,5(10)-triene-3,16α-diol 3-ethylether methanesulphonate (1:1) (salt)

Action of sodiummethoxide/ethyliodide on 17β-(N-formyl-N-methylamino)-oestra-1,3,5(10)-triene-3,16α-diol (ex Example XXVI (a)) afforded the corresponding 3-ethylether. Hydrolysis with methanol potassium hydroxide solution gave the corresponding 17β-methylamino-3,16α-diol 3-ethylether, which by treatment with methane-sulphonic acid was converted into the title compound, m.p. 244°–261° C., $[\alpha]_D + 47.1°$.

(b) 17β-Methylamino-oestra-1,3,5(10)-triene-3,16α-diol 3-n-propylether methanesulphonate (1:1) (salt)

A similar procedure as described in Example XXXVIII (a) using n-propyliodide instead of ethyliodide afforded the title compound, m.p. 218°–228° C., $[\alpha]_D + 45.7°$.

EXAMPLE XXXIX ent-17β-Methylamino-oestra-1,3,5(10)-triene-3,16α-diol ent-17β-Methylamino-oestra-1,3,5(10)-triene-3,16α-diol 3-methylether (5.0 g) was heated in 200 ml hydrobromic acid solution at 100° C. for 2.5 hours. Usual isolation after neutralisation gave 3.8 g of the title compound, m.p. 240°–244° C. (decomp.) and $[\alpha]_D - 47.5°$ (c 1.0 in D.M.S.O. (dimethylsulphoxide)).

EXAMPLE XL

17β-Methylamino-oestra-1,3,5(10)-triene-3,16α-diol 3-esters and their maleate salts Treatment of 17β-methylamino-oestra-1,3,5(10)-triene-3,16α-diol with benzylchloroformate in aqueous acetone containing potassium carbonate afforded the 17-benzylcarbamate.

Acetylation of the 17-benzylcarbamate with acetic acid anhydride in pyridine gave the 3-acetate. Hydrogenation in acetic acid over palladium on carbon smoothly decarboxylated the carbamate to give 17β-methylamino-oestra-1,3,5(10)-triene-3,16α-diol 3-acetate, which was isolated in the form of its maleate m.p. 194°–196° C., $[\alpha]_D + 33.6°$ (c 1.0 in ethanol).

Treatment of the 17-benzylcarbamate with sodium hydride in tetrahydrofuran and then with pivaloylchloride gave the 3-pivalate. Hydrogenation over palladium on carbon in methanol gave 17β-methylamino-oestra-1,3,5(10)-triene-3,16α-diol 3-pivalate. Maleate, m.p. 196°–199° C., $[\alpha]_D + 35.6°$ (c 1.0 in ethanol).

A similar procedure while replacing pivaloylchloride with propionylchloride gave 17β-methylamino-oestra-1,3,5(10)-triene-3,16α-diol 3-propionate. Maleate, m.p. 182°–185° C., $[\alpha]_D + 33.8°$ (c 1.0 in ethanol).

We claim:

1. Steroids of the androstane and oestrane series selected from the group consisting of compounds having the formula I:

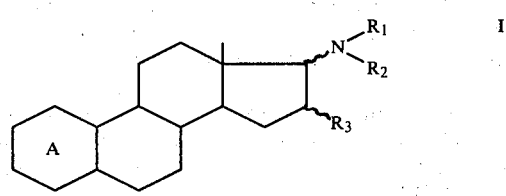

and pharmaceutically acceptable non-toxic acid additional salts thereof, wherein:

$R_1$ = H or hydrocarbyl of one to six carbon atoms;
$R_2$ = H or hydrocarbyl of one to six carbon atoms;
$R_3$ = a free, esterified or etherified hydroxyl group;

ring A, inclusive of carbon atoms 6 and 9, has one of the following configurations:

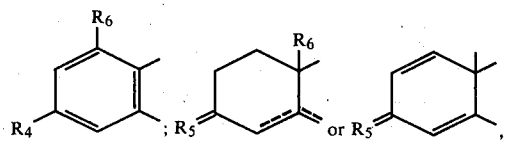

in which
$R_4$ = a free, esterified or etherified hydroxyl group;
$R_5$ = O or H($R_7$), wherein $R_7$ is a free, esterified or etherified hydroxyl group;
$R_6$ = H or methyl and
the dotted lines represent an optional double bond in the 4,5-position when $R_5$ is O or H($R_7$), or in the 5,6-position when $R_5$ is H($R_7$), and the enatiomers and racemates of these steroids.

2. Steroids of the androstane and oestrane series selected from the group consisting of compounds having the formula II:

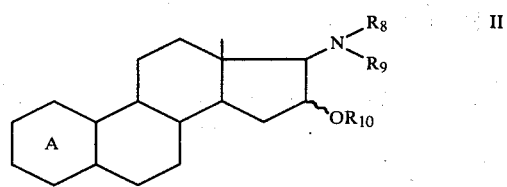

and pharmaceutically acceptable non-toxic acid additional salts thereof, wherein:

$R_8$ = H or methyl;
$R_9$ = H or methyl;
$R_{10}$ = H or lower alkanoyl of one to four carbon atoms;

ring A has one of the following configurations:

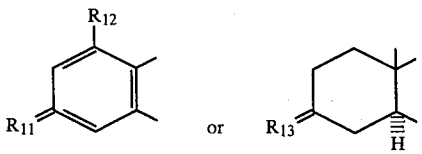

in which
- $R_{11}$ = OH, alkanoyloxy of one to six carbon atoms or alkoxy of one to four carbon atoms;
- $R_{12}$ = H or $CH_3$;
- $R_{13}$ = O, H($\beta$OH) or H($\beta$-alkanoyloxy of one to six carbon atoms); and the enantiomers and racemates of these steroids.

3. Pharmaceutical composition having anti-arrhythmic properties, comprising a pharmaceutically effective amount of one or more of the compounds of claim 1 or 2 in admixture with a usual pharmaceutical carrier.

4. A compound selected from the group consisting of 16$\alpha$-hydroxy-17$\beta$-methylamino-5$\alpha$-androstane-3-one maleate, 17$\beta$-methylamino-5$\alpha$-androstane-3$\beta$,16$\alpha$-diol maleate, 17$\beta$-amino-5$\alpha$-androstane-3$\beta$,16$\alpha$-diol maleate, 17$\beta$-methylamino-5$\alpha$-androstane-3$\beta$,16$\alpha$-diol 3-acetate hydrocloride, 17$\beta$-methylamino-androst-5-ene-3$\beta$,16$\alpha$-diol maleate, 16$\alpha$-hydroxy-17$\beta$-methylamino-androst-4-en-3-one maleate, 16$\alpha$-hydroxy-17$\beta$-methylene-androsta-1,4-dien-3-one maleate, 16$\beta$-hydroxy-17$\beta$-methylamino-5$\alpha$-androstan-3-one maleate, 17$\beta$-methylamino-5$\alpha$-androstane-3$\alpha$,16$\beta$-diol maleate, 16$\beta$-hydroxy-17$\alpha$-methylamino-5$\alpha$-androstan-3-one maleate, 17$\beta$-methylamino-oestra-1,3,5(10)-triene-3,16$\beta$-diol hydrochloride, 17$\beta$-methylamino-oestra-1,3,5(10)-triene-3,16$\beta$-diol hydronitrate, 17$\beta$-methylamino-oestra-1,3,5(10)-triene-3,16$\beta$-diol 3-methylether hydrochloride, 17$\beta$-methylamino-oestra-1,3,5(10)-triene-3,16$\alpha$-diol hydrochloride, 17$\beta$-methylamino-oestra-1,3,5(10)-triene-3,16$\alpha$-diol 3-methylether hydrochloride, 17$\beta$-methylamino-oestra-1,3,5(10)-triene-3,16$\alpha$-diol maleate, 17$\beta$-dimethylamino-oestra-1,3,5(10)-triene-3,16$\alpha$-diol maleate, 1-methyl-17$\beta$-methylamino-oestra-1,3,5(10)-triene-3,16$\alpha$-diol hydrochloride, 17$\beta$-ethylamino-oestra-1,3,5(10)-triene-3,16$\alpha$-diol maleate, 17$\beta$-amino-oestra-1,3,5(10)-triene-3,16$\alpha$-diol citrate, 17$\beta$-methylamino-oestra-1,3,5(10)-triene-3,16$\alpha$-diol methane-sulfonate, 17$\beta$-isopropylamino-oestra-1,3,5(10)-triene-3,16$\alpha$-diol citrate, 17$\beta$-dimethylamino-oestra-1,3,5(10)-triene-3,16$\alpha$-diol 3-acetate maleate, dl-17$\beta$-methylamino-oestra-1,3,5(10)-triene-3,16$\alpha$-diol 3-methylether hydrochloride, dl-17$\beta$-methylamino-oestra-1,3,5(10)-triene-3,16$\alpha$-diol hydrochloride, ent-17$\beta$-methylamino-oestra-1,3,5(10)-triene-3,16$\alpha$-diol 3-methylether hydrochloride, ent-17$\beta$-methylamino-oestra-1,3,5(10)-triene-3,16$\alpha$-diol hydrochloride, 17$\beta$-methylamino-oestra-1,3,5(10)-triene-3,16$\alpha$-diol 3-ethylether methanesulfonate, 17$\beta$-methylamino-oestra-1,3,5(10)-triene-3,16$\alpha$-diol 3-propylether methane-sulfonate, 17$\beta$-methylamino-oestra-1,3,5(10)-triene-3,16$\alpha$-diol 3-acetate maleate, 17$\beta$-methylamino-oestra-1,3,5(10)-triene-3,16$\alpha$-diol 3-propionate maleate, 17$\beta$-methylamino-oestra-1,3,5(10)-triene-3,16$\alpha$-diol 3-pivalate maleate, 17$\alpha$-methylamino-oestra-1,3,5(10)-triene-3,16$\beta$-diol 3-methylether hydrochloride, and 17$\beta$-amino-oestra-1,3,5(10)-triene-3,16$\beta$-diol 3-methylether hydrochloride.

5. A compound according to claim 1 wherein $R_1$ is methyl.

6. A compound according to claim 1 wherein $R_2$ is methyl.

7. A compound according to claim 2 wherein the group $OR_{10}$ is in the $\alpha$-position.

8. A compound according to claim 2 wherein $R_{11}$ is OH.

9. A compound according to claim 2 wherein $R_{13}$ is O.

* * * * *